US005453220A

United States Patent [19]
Swager et al.

[11] Patent Number: 5,453,220
[45] Date of Patent: Sep. 26, 1995

[54] CALIXARENE-BASED TRANSITION METAL COMPLEXES AND PHOTONIC DEVICES COMPRISING THE SAME

[75] Inventors: Timothy M. Swager, Wynnewood; Bing Xu, Philadelphia, both of Pa.

[73] Assignee: The Trustees of the University of Pennsylvania, Philadelphia, Pa.

[21] Appl. No.: 11,301

[22] Filed: Jan. 29, 1993

[51] Int. Cl.$^6$ .................................................. F21V 9/00
[52] U.S. Cl. .................... 252/582; 252/587; 359/328; 568/74; 568/75; 568/76; 568/77; 568/631; 568/632; 568/633; 549/346; 549/347; 540/450; 540/465; 540/467; 540/470; 556/1; 556/13
[58] Field of Search ................................ 252/582, 587, 252/589; 359/326, 328, 329; 568/631, 632, 633, 74, 75, 76, 77; 549/346, 347; 540/450, 465, 467, 470; 556/1, 13

[56] References Cited

U.S. PATENT DOCUMENTS

| | | | |
|---|---|---|---|
| 4,882,449 | 11/1989 | Harris | 556/419 |
| 5,114,601 | 5/1992 | Cook et al. | 252/25 |
| 5,205,946 | 4/1993 | Cook et al. | 252/25 |
| 5,210,216 | 5/1993 | Harris et al. | 548/518 |
| 5,344,467 | 9/1994 | Huang et al. | 44/358 |

OTHER PUBLICATIONS

Heesink et al., Appl. Phys. Lett., vol. 62, No. 17, pp. 2015–2017, (1993).

*Primary Examiner*—Philip Tucker
*Attorney, Agent, or Firm*—Woodcock, Washburn, Kurtz, Mackiewicz & Norris

[57] ABSTRACT

Calixarene-based, noncentrosymmetric transition metal complexes that exhibit large second order nonlinear optical and related electro-optical properties are provided, as are materials and devices comprising the same.

19 Claims, 4 Drawing Sheets

CALIXARENE-BASED TRANSITION METAL COMPLEXES AND PHOTONIC DEVICES COMPRISING THE SAME

GOVERNMENT SUPPORT

This work has been supported by the Office of Naval Research under grant N00014-92-J-1416.

FIELD OF THE INVENTION

This invention relates to materials that are useful in the fabrication of electro-optical, second harmonic generating, electro-acoustic, waveguide, fiber, semiconductor, and other useful photonic devices. In particular, this invention is concerned with materials that exhibit second order nonlinear optical properties.

BACKGROUND OF THE INVENTION

Nonlinear optical properties are the basis of newly emerging photonics technologies in which light works with, or even replaces, electrons in applications traditionally carried out by microelectronics. Second-order nonlinear optical processes, in which the response is proportional to the square of applied electric fields, arise only in materials that are noncentrosymmetric. As a result, the design of molecules which crystallize or can be organized into noncentrosymmetric structures is an active area of materials research. Approaches to the formation of noncentrosymmetric molecular structures include the attachment of chiral groups, the incorporation of molecules into host materials, the formation of Langmuir-Blodgett or synthetic multilayer films, and the poling of polymers. However, all of these methods have limitations with regard to chromophore density, degree of orientation, preparation of bulk optical-quality samples, ease of device fabrication, transparency, long term and thermal stability, and phase matching.

There exists a need in the art for new methodologies for the production of noncentrosymmetric structures for future nonlinear optical technologies.

OBJECTS OF THE INVENTION

It is one object of the present invention to provide novel noncentrosymmetric structures.

It is another object of the invention to provide novel materials that exhibit nonlinear optical properties.

It is yet another object to provide materials that exhibit second order nonlinear optical properties.

It is another object to provide nonlinear optical materials that incorporate bowlic liquid crystals.

It is a further object to provide nonlinear optical materials that incorporate bowlic transition metal/calixarene complexes.

SUMMARY OF THE INVENTION

These and other objects are satisfied by the present invention, which provides noncentrosymmetric materials that exhibit large second order nonlinear optical and related electro-optical properties. These materials are based on a new class of liquid crystalline compounds and related molecular assemblies that have pyramidic, calixarene-based, transition metal complexes as core groups.

In certain embodiments, the metal complexes have formulas (1) and (2) wherein X and Y, respectively, are tetravalent and trivalent groups that are electron-withdrawing relative to hydrogen and $R_{B1}$, $R_{B2}$, and $R_{A3}$ are, independently, H or a group that is electron-donating relative to hydrogen. In other embodiments, X and Y, respectively, are tetravalent and trivalent groups that are electron-donating relative to hydrogen and $R_{B1}$, $R_{B2}$, and $R_{B3}$ are, independently, H or a group that is electron-withdrawing relative to hydrogen.

(1)  (2)

In both embodiments Z is group Vb or group VIb heteroatom or a substituted group Vb or group VIb heteroatom, Q has formula $R_{A1}$, $R_{A1}$—$R_{A2}$, $R_{A1}$—$R_{A2}$—$R_{A3}$, or $R_{A1}$—$R_{A2}$—$R_{A3}$—$R_{A4}$ wherein each $R_A$ is, independently, O, S, N—$R_L$, or CH—$R_L$, and each $R_L$ is, independently, H, halogen, $C_{1-20}$ alkyl, or $C_{6-30}$ aryl. Preferred tetravalent complexes are those wherein X has formula M-L where M and L are selected such that:

M is W or Mo and L is O or N—$R_L$; or

M is Re or Tc and L is N; or

M is V, Ta, or Nb and L is O—$R_L$.

Preferred trivalent complexes are those wherein Y has formula M-L where M and L are selected such that:

M is Mo, Cr, and W and L is N; or

M is V, Ta, or Wa and L is O or N—$R_L$.

The present invention further provides materials and devices that exhibit sensible nonlinear optical effects, as well as processes for preparing such materials and devices. In general, the devices comprise a layer that contains at least one compound of the invention disposed upon a substrate. The layer can contain the compound in pure or substantially pure form or in combination with other chemical compounds such as known synthetic organic polymers.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

It has been found in accordance with the present invention that noncentrosymmetric systems containing certain calixarene-based metal complexes exhibit sensible nonlinear optical effects, particularly second order nonlinear optical effects. In these systems, noncentrosymmetry is believed to be promoted at the molecular level by the shape of the complexes and a head-to-tail self-ordering system promoted thereby. Bulk noncentrosymmetry is produced by poling these organized assemblies with electric fields.

In preferred embodiments, the calixarene-based compounds of the invention have formulas (1) and (2):

(1)

(2)

wherein X and Y, respectively, are tetravalent and trivalent groups that are electron-withdrawing relative to hydrogen, Z is group Vb or group VIb heteroatom or a substituted group Vb or group VIb heteroatom, and $R_{B1}$, $R_{B2}$, and $R_{B3}$ are, independently, H or a group that is electron-donating relative to hydrogen.

Numerous examples of electron-donating and electron-withdrawing groups are well-known to those skilled in the art. Further, electron-donating and electron-withdrawing groups can be identified through routine experimentation (e.g., substitution for hydrogen in a molecule and testing of any resultant inductive effects). Representative electron-donating groups include alkyl groups, alkenyl groups, aryl groups, aryl groups substituted with alkyl groups, alkylamino groups, $NH_2$, alkoxyl groups, OH, alkylthio groups, SH, and/or —OC(O)-(alkyl) groups. Representative electron-withdrawing groups include aryl groups substituted with one or more groups selected from $N\text{-}(alkyl)_3^+$, $S\text{-}(alkyl)_2^+$, $NH_3^+$, $NO_2$, $SO_2\text{-}(alkyl)$, CN, $SO_2\text{-}(aromatic)$, C(O)OH, F, Cl, Br, I, C(O)O-(alkyl), C(O)-(alkyl), and/or CHO.

$R_{B1}$, $R_{B2}$, and $R_{B3}$ preferably are electron-donating, more preferably alkyl groups having 1 to about 20 carbon atoms, alkenyl groups having 2 to about 20 carbon atoms, aryl groups having 6 to about 30 carbon atoms, and alkyl-, alkenyl-, and aryl-substituted amine groups. In accordance with this invention, alkyl groups preferably have 1 to about 12 carbon atoms, alkenyl groups have from 2 to about 12 carbon atoms, and alkyl groups have from 6 to about 14 carbon atoms. It will be recognized that the terms alkyl, alkenyl, and aryl include straight-chain, branched-chain, and cyclic structures, as well as structures wherein alkyl, alkenyl, or aryl groups or heteroatoms or heteroatom-containing substituents are inserted into or appended to the carbon backbone of an alkyl, alkenyl, or aryl group. Representative heteroatoms include N, P, O, S, Se, Te, and halogens, and combinations thereof (e.g., $NO_3$, $CF_3$). Preferred aryl electron-donating groups for attachment at, for example, position $R_{B2}$ have formula (3a–d), wherein $R_1$, $R_2$, and $R_3$ are, independently, H, $C_{1\text{-}20}$ alkyl, O—$C_{1\text{-}20}$ alkyl, or N—$(C_{1\text{-}20}$ alkyl$)_2$. It will be recognized, however, that $R_{B1}$, $R_{B2}$, and $R_{B3}$ also can be electron-withdrawing.

X and Y preferably are electron-withdrawing and are tetra- and trivalent transition metal-containing moieties having general formula M-L. One representative electron-withdrawing group has formula (4a). For compounds having formula (1), M and L preferably are selected such that: M is W or Mo and L is O or N—$R_L$; or M is Re or Tc and L is N; or M is V, Ta, or Nb and L is O—$R_L$. Preferred compounds are those wherein: M is W or Mo and L is O; M is Re and L is N; and M is V and L is O—$R_L$. For compounds having formula (2), M and L are selected such that: M is Mo, Cr, or W and L is N; or M is V, Ta, or Nb and L is O or N—$R_L$. Compounds wherein M is W and L is N or M is V and L is O are preferred. X and Y also can be electron-donating groups having, for example, formula (4b).

The X and Y groups are appended to a derivatized calixarene via heteroatom Z. X and Y can be bound to Z via an covalent or ionic bond or some weaker intermolecular interaction. Z preferably is O, S, —NH—, —$NH_2^+$—, or —N=.

Figure 1:
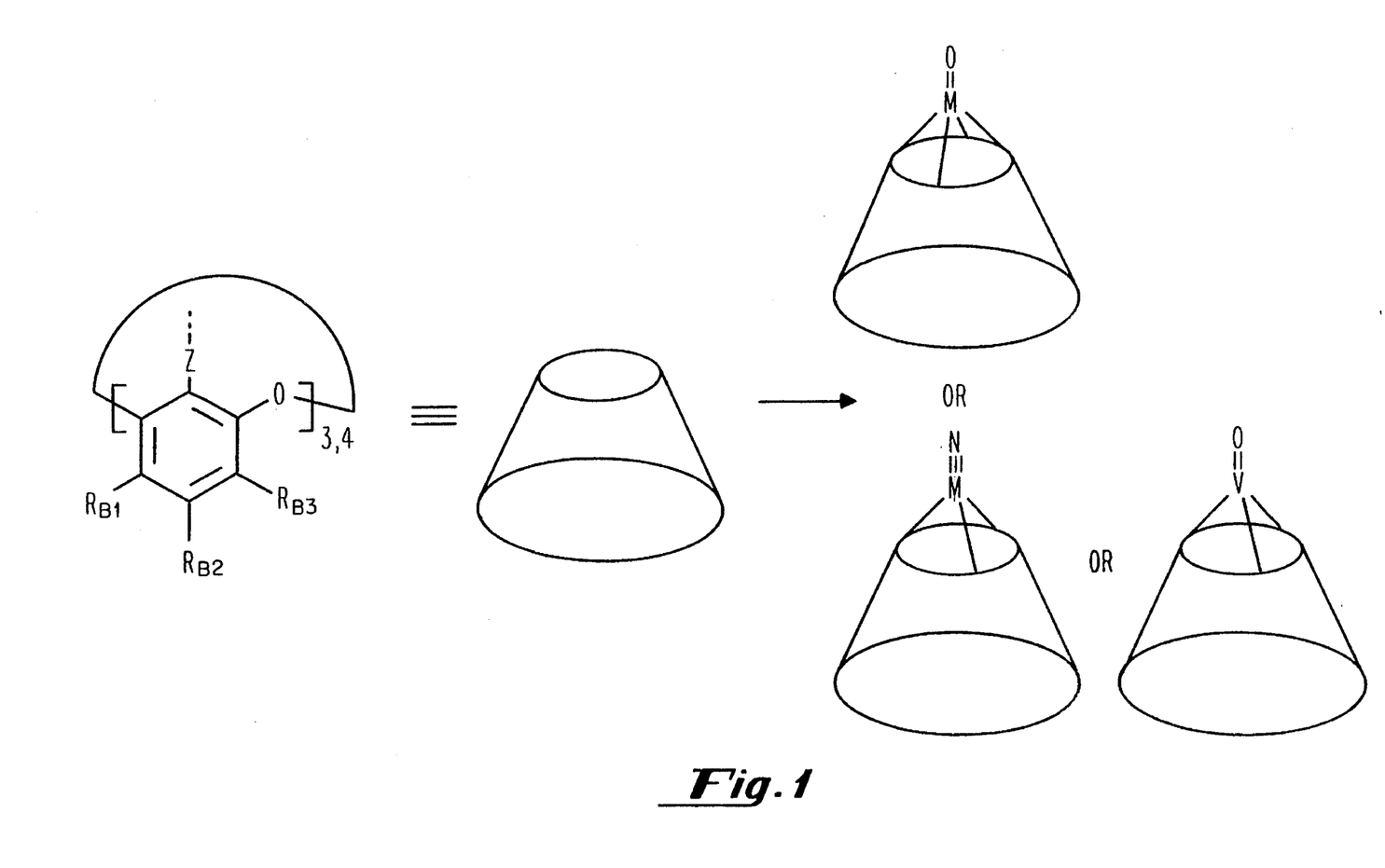
FIG. 1 shows the conical conformation of calix[3]arenes and calix[4]arenes and transition metal complexes thereof.

As shown in FIG. 1, the calixarenes and calixarene-based compounds of the invention assume a generally conical conformation. In fact, x-ray structural analysis reveals that coordination of these bowlic compounds to transition metals usually reinforces their conical conformation, which provides a strong geometric influence promoting columnar, head-to-tail alignment on a molecular level. Such alignment is exemplified in FIG. 2, in which the oxomolybdenum "head" 20a of mesogen 20 is positioned within the cavity-defining calixarene "tail" 22b of adjacent mesogen 22. Head 22a is, in turn, positioned within tail 22b of the next adjacent mesogen, 24.

A wide variety of functionalized calix[3]arenes and calix[4]arenes suitable for use in accordance with the invention are known in the art, as are methods for their preparation. Indeed, the organic chemistry of calixarenes is extensive (see, e.g., C. D. Gutsche, *Calixarenes*, Royal Society of Chemistry (1989); *Calixarenes: A Versatile Class of Macroscopic Compounds*, J. Vicens and V. B. Klewer, eds., Academic Publishers (1991); Cram, *Science* 1983, 219, 1177). A number of calixarene derivatives are even commercially available from Aldrich Chemical Company, Milwaukee, WI 53233.

Figure 3:
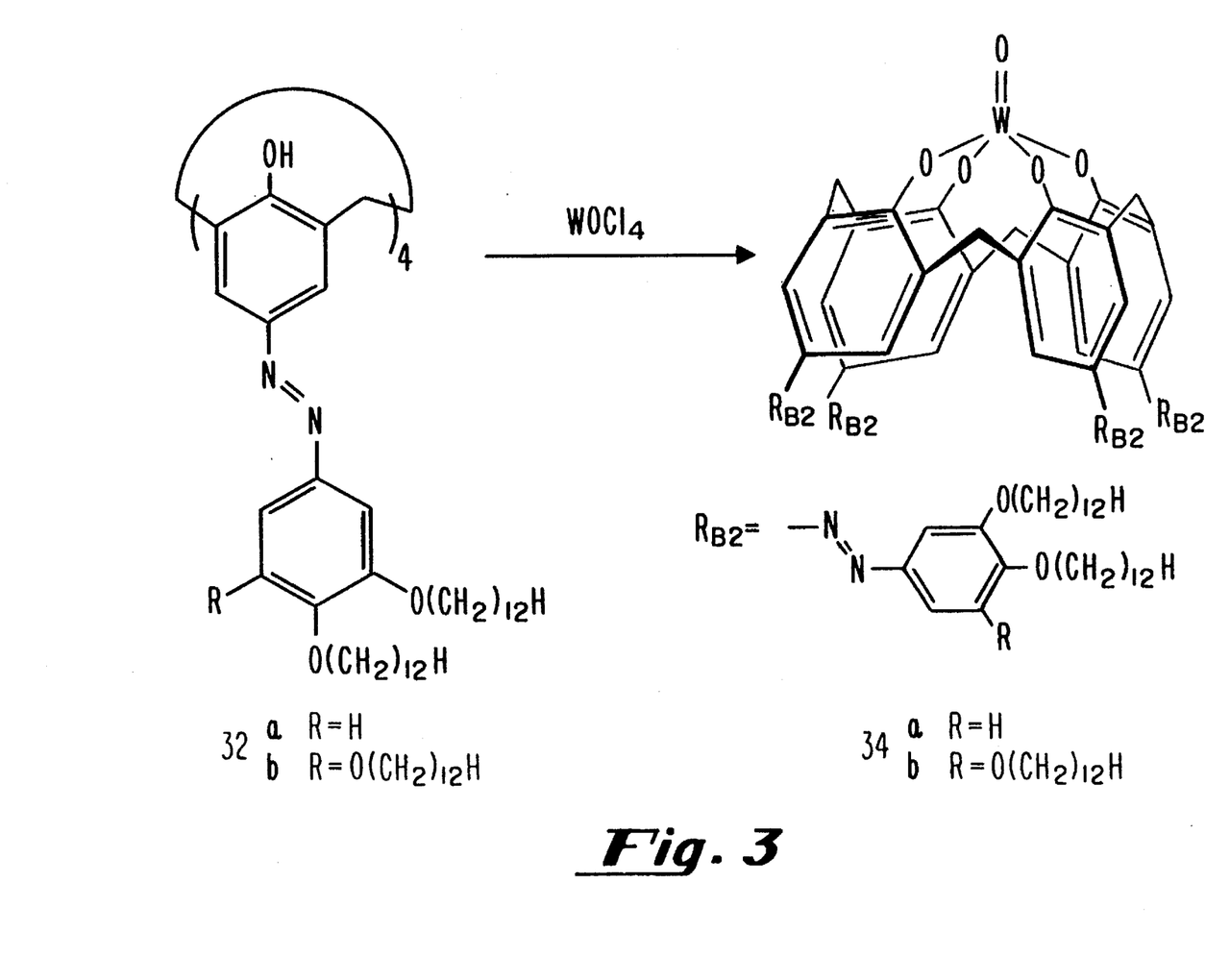
FIG. 3 shows a representative complexation procedure according to the invention.

The calixarene complexes of the invention typically are prepared by reacting such functionalized calixarenes with transition metal salts under conditions effective to form the desired —Z—M—bond. For example, FIG. 3 shows reaction of a phenolic calix[4]arene 32 with $WOCl_4$ to form tungsten-oxo complex 34a (see Example 2). Numerous other preparative processes are known in the art. (see. e.g., Corazza, et al., *Inorg. Chem.* 1991, 30, 4465; Corazza, et al., *J. Chem. Soc., Chem. Comm.* 1990, 640). Other Z groups bearing protons or electropositive reactive groups (e.g., Na, Li, $SIR_3$) will also react with transition metal salts to form Z-M bonds.

Capping 32a,b with a tungsten-oxo group to form 34a,b produces a mesogen with a rigid bowl conformation. This conformation promotes liquid crystallinity. As shown in Scheme 1, compounds 34a,b both display columnar mesophases (M, $M_1$, and $M_2$) which are stable over a wide temperature range. The M to isotropic transition enthalpy for 34a is fairly small (1.5 Kcal/mol) indicating that this mesophase is likely a disordered phase with liquid-like correlation between mesogens. Cooling the isotropic phase of 34a produces a texture for M characteristic of a columnar phase. Complex 34b displays two columnar phases $M_1$ and $M_2$, and the additional four sidechains lowers the clearing point to give a stable isotropic phase. The $M_2$—I transition enthalpy for 34b is 5.1 Kcal/mol, a value considerably greater than the isotropic transition observed for 34a. Miscibility studies indicate that M and $M_2$ have different structures. Slow cooling the $M_2$ phase of 34a produces a texture with digitized contours, leaf patterns, and large regions of uniform extinction. The large areas of extinction suggest a uniaxial structure, and the observation of digitized stars with six-fold symmetry and 120° facets confirms a hexagonal arrangement of the columns in $M_2$. Birefringence decreases with increasing temperature for both 34a and 34b, and there is a particularly large change between the mesophase and the crystal phase. The large $M_2$-I transition enthalpy for 34b and the spherulitic growth of the phase suggests that the mesogens are ordered in the columns. Therefore, $M_2$ can be characterized as a bowlic $D_{ho}$. The small enthalpy of the $M_1$–$M_2$ phase transition and the absence of textural changes suggests that the structure of $M_1$ and $M_2$ are closely related.

interactions with Lewis bases. A number of compounds can serve as guests. For example, infrared spectroscopy confirms that dimethylformamide (DMF) forms a Lewis base complex. The W=O band undergoes a characteristic shift from 1074 $cm^{-1}$ to 990 $cm^{-1}$ with DMF complexation. Likewise, the C=O band of the DMF of the host-guest complex in methylene chloride solution occurs at 1645 $cm^{-1}$, which is 25 $cm^{-1}$ lower in energy than uncomplexed DMF in methylene chloride. The host-guest complexes exhibit more complicated $H^1$ NMR spectra, with signals assigned to DMF at 7.81δ, 1.55δ, 1.36δ, and 0.58δ($CDCl_3$) and at 8.05δ, 0.41δ, 0.29δ, and 0.28δ($C_6D_6$). The relative intensities of these signals were variable depending on sample history. However, treatment of host-guest complexes with pyridine or diisopropylamine results in quantitative liberation of one equivalent of DMF with signals at 7.99δ, 2.93δ, and 2.86δ($CDCl_3$). In addition, one of the calix[4]arene methylene resonances was sensitive to guests, with a shift from 4.80δ to 4.85δ($CDCl_3$) with a DMF guest. The large up-field shift of the DMF protons is consistent with the shielding environment provided by the cavity.

The most dramatic consequence of host-guest complexation is its effect upon the mesomorphic behavior of the complexes. While 34a exhibits a discotic mesophase from 135° C. to 330° C., the DMF-34a host-guest complex melts directly to an isotropic phase at 115°C. (ΔH =12.3 Kcal/mol). Likewise, the 34b-DMF host-guest complex melts to form an isotropic phase at 84° C. Complexes with pyridine guests exhibit isotropic transition at the same temperature, indicating that a filled cavity is more important than the nature of the guest. With further heating, (200°–250° C.), the DMF slowly dissociates to form the discotic phase.

The depression of the isotropic phase through host-guest complexation allows the formation of a texture for 34a consisting of well defined cyclides with a tangential orientation of the optic axis characteristic of columnar phases. Observation of these textures with a λ plate shows that 34a exhibits unusual temperature dependent changes in the optic sign. The K phase is optically positive. However, in heating cycles at temperatures just above the K-M transition (<20° C.), the optic sign becomes negative. At higher temperatures the M phase becomes optically positive again. This transition to an optically negative material is not observed on cooling and is most likely due to conformational preferences of the azophenyl groups.

Figure 2:
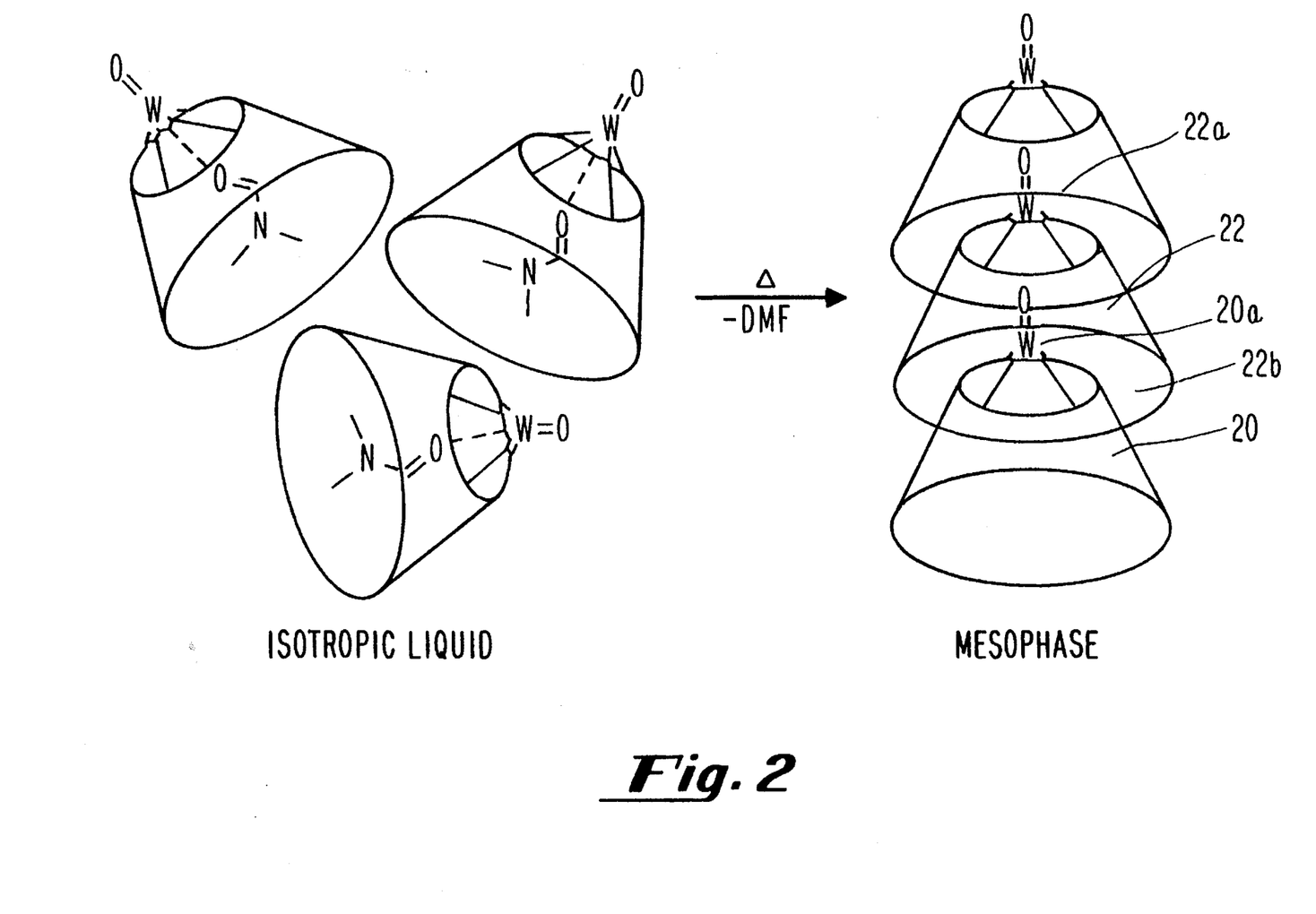
FIG. 2 shows isotropic and mesophase orientation of certain compounds of the invention.

The deleterious effect of a DMF or pyridine guest on the mesophase stability, combined with the columnar structure of the mesophases, suggests that the bowlic cores exhibit a head-to-tail alignment whereby tungsten-oxo groups protrude into the cavity of the neighboring mesogen, as shown in FIG. 2. The bowlic $D_{ho}$ phase of 34b is important since triangular symmetry dictates that the polar head-to-tail organization in the column must result in ferroelectric interco- Scheme 1

The combination of the rigid cavity and the Lewis acidic nature of the square pyramidal tungsten produces a pronounced tendency for 34a and 34b to display host-guest lumnar order or in a frustrated phase with random polarization. Additionally, the depression of the isotropic point through host-guest complexation provides a route to a low viscosity state at reduced temperatures. This feature will allow for poling of very high-melting bowlic complexes to produce noncentrosymmetric materials with high temporal stability.

Figure 4:
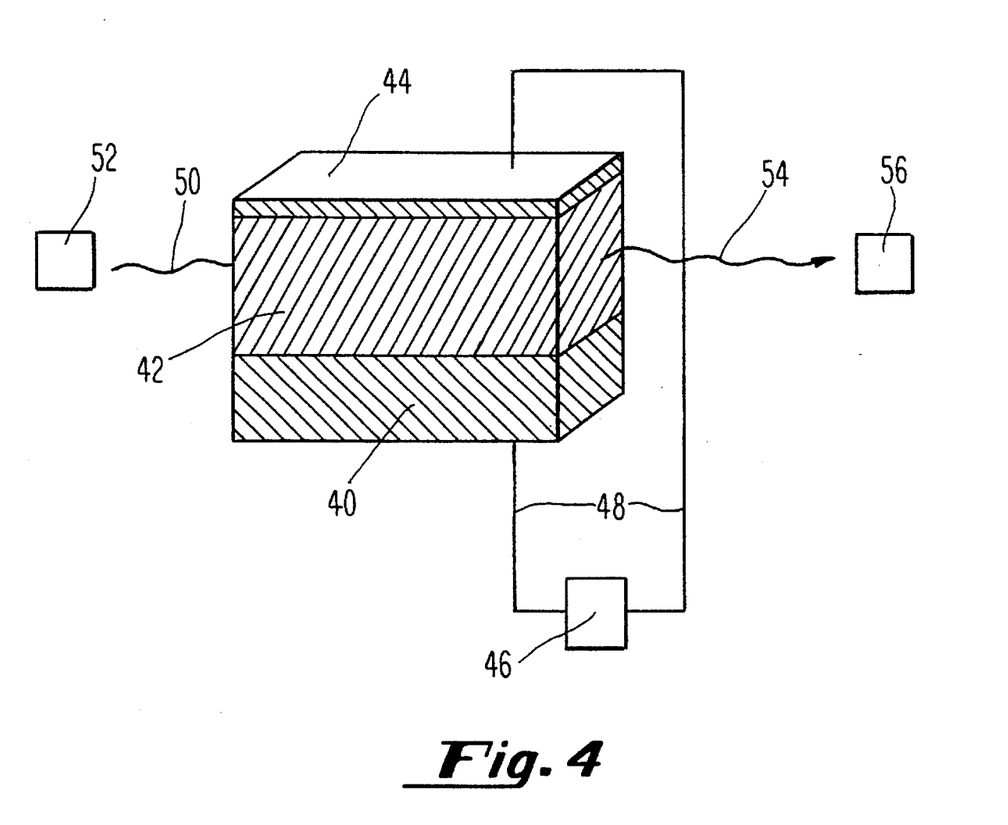
FIG. 4 shows a photonic device comprising a substrate and a layer that contains a compound of the invention.

The compounds of the invention find use in a wide variety of devices, including electro-optical, second harmonic generating, electro-acoustic, waveguide, semiconductor, and other photonic or electronic devices. As shown in FIG. 4, devices according to the invention generally comprise a dielectric or some other substrate 40 and a layer 42, disposed on the substrate, comprising at least one compound of the invention. Useful substrates include semiconductors such as silicon gallium arsenide or insulators such as glass or plastic. Alteratively, layer 42 can contain a compound of the invention in combination with one or more synthetic organic polymers. In certain embodiments, for example, the layer can include synthetic organic polymer or precursors thereof (e.g., monomers, catalysts, and sensitizers) in admixture with a compound having formula (1) or (2). It is believed that the compounds of the invention can be mixed with virtually any synthetic organic polymer or polymer precursor system known in the art. Representative synthetic organic polymers include polyimides, polyacrylates, polymethacrylates, polyesters, polycarbonates, polystyrenes, polyolefins, and polyvinyl ethers.

The coating of a substrate with a material comprising a compound of the invention can be accomplished by any means known in the art, preferably by spin-coating, role-coating, or physical vapor deposition. See, e.g., L. I. Maissel and R. Glang, *Handbook of Thin Film Technology*, McGraw-Hill (1970); Satas, *Coating Technology Handbook*, Marcel Dekker (1991). The materials used to form layer 42 can further include other moieties such as, for example, pigments, dyes, filters and dopants.

Polymerization and/or crosslinking of a layer following its deposition on a substrate can be accomplished in any of the ways known to those skilled in the art. For example, certain polymerizations can be effected by simple heating in the presence of a suitable initiator or by the incidence of light or some other form of electromagnetic energy in the presence or absence of a sensitizer. The latter procedure is preferred due to the ability of those in the art to effect selective, patterned polymerization through the use of, for example, removable masking agents. As will be recognized, devices incorporating appropriately arrayed patterns of polymer can be employed in microcircuitry and other applications.

In embodiments such as shown in FIG. 4, certain devices of the invention comprise a conductor superstrate 44 disposed on layer 42, control means 46, and contacts 48 attached to substrate 40 and superstrate 44. This arrangement allows an input light signal 50 from source 52 to be operated upon by virtue of a changing electric field within layer 42 generated by control means 46 in concert with contacts 48. Altered or "operated" light signal 54 is directed away from the layer to a suitable detector 56. A wide variety of devices fitting this general description are well-known to those skilled in the art. See, e.g., Dorn, et al., *Advanced Materials* 1992, 4, 464.

Additional objects, advantages, and novel features of this invention will become apparent to those skilled in the art upon examination of the following examples thereof, which are not intended to be limiting.

EXAMPLE 1

Preparation of Compound 32a

A methylene chloride (250 ml) solution of 1,2-didodecanoxylbenzene (20 g, 64.8 mmol) was reacted with dry silica gel (80 g, saturated by 8N, 200 ml $HNO_3$) at room temperature for 5 minutes and then filtered. After evaporation of the solvent, the resulting solid recrystallized from tetrahydrofuran/methanol (THF/MeOH) to produce 1,2-didodecanoxy-4-nitrobenzene (18 g, 82%) as white solid $^1H$ NMR ($CDCl_3$, 250 MHz, ppm) d 7.82 (d, Ph, 1H), 7.65 (s, Ph, 1H), 6.82 (d, Ph, 1H), 4.00(m, $OCH_2$, 4H), 2.0–0.8(m, alkyl).

1,2-Didodecanoxy-4-nitrobenzene (10 g, 20.4 mmol) was then dissolved in ethanol (100 ml), followed by addition of hydrazine (4ml) and graphite (8 g). The mixture was then refluxed for 24 hours and filtered. The filtrate was given a hexane/water work-up and the hexane fraction was dried over $MgSO_4$ and evaporated to produce 1,2-didodecanoxy-4-amino benzene as white solid (8.9 g, 95%). $^1H$ NMR ($CDCl_3$) d 7.02(s, Ph, 1H) 6.96 (d, Ph, 1H), 6.69 (d, Ph, 1H), 3.97 (m, $OCH_2$, 4H), 2.0–0.8 (m, alkyl ).

Hydrochloric acid (2.7 ml, 37%) and $NaBF_4$ (3.0 g) were added to a $H_2O$/THF (250 ml/30 ml) suspension of 1,2-didodecanoxy-4-amino benzene (5.72 g, 12.4 mmol) . The resultant mixture was stirred at room temperature for 1.5 hours and cooled to 0° C. $NaNO_2$ (0.86 g, 12.4 mmol) then was added and the mixture stirred for 12 hours. 1,2-didodecanoxyl-4-diazobenzene tetraflouroborate was then isolated by filtration and recrystallized from acetone/ether as white needle crystals (5.8 g, 84%). $^1H$ NMR ($CD_3COCD_3$) 8.55 (d, ph, 1H), 8.21 (s, Ph, 1H), 7.55 (d, Ph, 1H), 4.38 (t, $OCH_2$, 2H) 4.16 (t, $OCH_2$, 2H),.2.0–0.8 (m, alkyl).

1,2-Didodecanoxyl-4-diazo-benzene tetraflouroborate (1.02 g, 1.8 mmol) , calix[4]arene (0.17 g, 0.4 mmol), and pyridine (0.2 ml) were added to THF (20 ml), and stirred at 25° C. for 12 hours. The mixture was filtered and methanol was added to the filtrate until it appeared cloudy, The resultant mixture was cooled at 0° C. for 16h. 32a was then isolated as yellow needle crystals (0.85 g, 91%). $^1H$ NMR ($CDCl_3$) 10.22 (br. d, OH, 4H), 7.73 (s, Ph, 2H), 7.46 (d, PH, 1H), 7.38 (s, Ph, 1H), 6.91 (d, Ph, 1H), 4.35 (br, $PhCH_2$, 1H), 4.02 (m, $OCH_2$, 4H), 3.80(br, $PhCH_2$,1H), 2.0–0.8(m, alkyl).

EXAMPLE 2

Preparation of 34a (DMF complex)

This reaction was carried out under an atmosphere of argon. Toluene was dried and vacuum distilled from sodium benzophenone ketyl prior to use.

A toluene (10 ml) suspension of $WOCl_4$ (0.152 g, 0.44 mmol) was reacted with 32a (1.027 g, 0.44 mmol). The suspension was refluxed for 16 hours and the resultant orange-brown solution then evaporated. The solid was recrystallized with THF/DMF/MeOH (1:2:3), to give 34a a yellow solid (0.96 g, 86%). The yellow solid can be recrystallized from DMF and obtained as yellow needle crystals. $^1H$ NMR (C6D6) d 7.97 (s, Ph, 2h), 7.91 (s, Ph, 1H), 7.86 (d, Ph, 1H), 6.72 (d, Ph, 1H), 4.92 (d, $PhCH^2$, 1H) 4.27 (s, formyl, 1H), 3.86 (t, $OCH_2$, 2H) 3.68 (t, $OCH_2$, 2H), 3.29 (d, $PhCH_2$, 1H), 2.0–0.8 (m, alkyl), 0.40 (s, $CH_3$, 3H), 0.26 (s, $CH_3$, 3H).

Example 3

Preparation of Complex Having Formula (1) Wherein Z=O, X has formula (4b), $R_{B1}$ and $R_{B3}$ are H, and $R_{B2}$ is 1,2-Didodecanoxyl-4-diazo Benzene This reaction was carried out under an atmosphere of argon. Methylene chloride was dried with $P_2O_5$ and vacuum distilled prior to use.

4-Morpholinoaniline (1 g, 5.61 mmol) was dissolved in dry THF (25 ml). N-BuLi (1.41M, 8.8 ml) was added dropwise at 0° C. over 5 minutes and the solution changed from brown to yellow. After stirring for 2.5 hours while warming to room temperature, trimethylsilyl chloride (97%, 1.62 ml) was added, followed by stirring at room temperature for 12 hours. Evaporation of the solvent gave a yellow solid which was sublimed at $10^{-4}$ torr to produce pure 4-morpholino-N,N-bistrimethylsilyl aniline as white solid (1.32 g, 73%). $^1$H NMR ($CDCl_3$) 6.75 (s, Ph, 4H), 3.81 (t, $CH_2$, 4H), 3.05 (t, $CH_2$, 4H), 0.03 (s, TMS, 18H).

Tungsten (VI) oxocalix[4]arene (0.1167 g, 0.19 mmol) and 4-morpholino-N,N-bistrimethylsilyl aniline (0,077 g, 024 mmol) were dissolved in methylene chloride (10 ml), and refluxed 18h. The solution changed from red to orange. Evaporation of the solvent gave 4b (about 80% yield) which was analyzed by FABMS. M+: calcd. 779, found 779.

EXAMPLE 4

Preparation of Complex Having Formula (1) Wherein Z=O, X has formula Re≡N, $R_{B1}$ and $R_{B3}$ are H, and $R_{B2}$ is 1,2-Didodecanoxyl-4-diazo Benzene

This reaction is carried out under an atmosphere of argon. Toluene is dried and vacuum distilled from sodium benzophenone ketyl prior to use.

A toluene (10 ml) suspension of $ReCl_5$ (0.44 mmol) is reacted with 32a (1.0270 g, 0.44 mmol). The suspension is refluxed for 16 hours and evaporated, and the resulting material dissolved in DMF (10 ml). Following addition of sodium azide (0.44 mmol), the mixture is refluxed for 3 hours. The solution is then irradiated with a mercury arc lamp for 1 hour and the product isolated by recrystallizations from THF/DMF/MeOH (1:2:3).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having formula:

wherein:

Z is group Vb or group VIb heteroatom

Q has formula $R_{A1}$, $R_{A1}$—$R_{A2}$, $R_{A1}$—$R_{A2}$—$R_{A3}$, or $R_{A1}$—$R_{A2}$—$R_{A3}$—$R_{A4}$ wherein each $R_A$ is, independently, O, S, N—$R_L$, or CH—$R_L$, wherein only one $R_A$ is O or S;

$R_L$ is H, halogen, $C_{1-20}$ alkyl, or $C_{6-30}$ aryl; and

X and $R_{B1}$, $R_{B2}$, and $R_{B3}$ are selected such that:

(a) X is a tetravalent group that is electron-donating relative to hydrogen; and $R_{B1}$, $R_{B2}$, and $R_{B3}$ are, independently, H or a group that is electron-withdrawing relative to hydrogen; or (b) X is a tetravalent group that is electron-withdrawing relative to hydrogen; and $R_{B1}$, $R_{B2}$, and $R_{B3}$ are, independently, H or a group that is electron-donating relative to hydrogen.

2. The compound of claim 1 wherein Z is O, S, NH, $NH_2$, or N.

3. The compound of claim 1 wherein X has formula M-L where M and L are selected such that:

M is W or Mo and L is N—$R_L$; or

M is Re or Tc and L is N; or

M is V, Ta, or Nb and L is O—$R_L$.

4. The compound of claim 3 wherein: M is W or Mo and L is O; or M is Re and L is N; or M is V and L is O—$R_L$.

5. The compound of claim 1 wherein each $R_B$ is, independently, $C_{1-20}$ alkyl, $C_{2-20}$ alkenyl, $C_{6-30}$ aryl, N—$R_{B'}$, or O—$R_{B'}$, wherein $R_{B'}$ is $C_{1-20}$ alkyl, $C_{2-20}$ alkenyl, or $C_{6-30}$ aryl.

6. The compound of claim 5 wherein $R_{B2}$ has formula (3a–d):

wherein $R_1$, $R_2$ and $R_3$ are, independently, H, $C_{1-20}$ alkyl, O—$C_{1-20}$ alkyl, or N—$(C_{1-20}$ alkyl$)_2$.

7. The compound of claim 1 wherein at least two molecules of said compound are aligned in a head-to-tail fashion.

8. The compound of claim 7 wherein X has formula M-L where M and L are selected such that M is W or Mo and L is O or N.

9. A compound having formula:

wherein:

Z is group Vb or group VIb heteroatom;

Q has formula $R_{A1}$, $R_{A1}$—$R_{A2}$, $R_{A1}$—$R_{A2}$—$R_{A3}$, or $R_{A1}$—$R_{A2}$—$R_{A3}$—$R_{A4}$ wherein each $R_A$ is, independently, O, S, N—$R_L$, or CH—$R_L$, wherein only one RA is O or S;

$R_L$ is H, halogen, $C_{1-20}$ alkyl, or $C_{6-30}$ aryl; and

Y and $R_{B1}$, $R_{B2}$, and $R_{B3}$ are selected such that:
(a) Y is a trivalent group that is electron-donating relative to hydrogen; and $R_{B1}$, $R_{B2}$, and $R_{B3}$ are, independently, H or a group that is electron-withdrawing relative to hydrogen; or
(b) Y is a trivalent group that is electron-withdrawing relative to hydrogen; and $R_{B1}$, $R_{B2}$, and $R_{B3}$ are, independently, H or a group that is electron-donating relative to hydrogen.

10. The compound of claim 9 wherein Z is O, S, NH, $NH_2$, or N.

11. The compound of claim 9 wherein Y has formula M-L where M and L are selected such that:

M is Mo, Cr, and W and L is N; or

M is V, Ta, or Wa and L is O or N—$R_L$.

12. The compound of claim 11 wherein M is W and L is N or M is V and L is O.

13. The compound of claim 9 wherein each $R_B$ is, independently, $C_{1-20}$ alkyl, $C_{2-20}$ alkenyl, $C_{6-30}$ aryl, N—$R_{B'}$, or O—$R_{B'}$ wherein $R_{B'}$ is $C_{1-20}$ alkyl, $C_{2-20}$ alkenyl, or $C_{6-30}$ aryl.

14. The compound of claim 13 wherein $R_{B2}$ has formula (3a–d):

(3a)

(3b)

(3c)

(3d)

wherein $R_1$, $R_2$, and $R_3$ are, independently H, $C_{1-20}$ alkyl, O—$C_{1-20}$ alkyl, or N—$(C_{1-20}$ alkyl $)_2$.

15. The compound of claim 9 wherein at least two molecules of said compound are aligned in a head-to-tail fashion.

16. A device that exhibits at least one sensible, second order nonlinear optical effect, comprising:
a substrate; and
at least one layer on said substrate, said layer including at least one compound according to claims 1 or 9.

17. A composition that exhibits at least one sensible, second order nonlinear optical effect, comprising synthetic organic polymer and at least one compound according to claims 1 or 9.

18. A process for preparing a device that exhibits at least one sensible, second order nonlinear optical effect, comprising the steps of:
providing a substrate; and
placing upon said substrate at least one layer that includes at least one compound according to claims 1 or 9.

19. A process for preparing a composition that exhibits at least one sensible, second order nonlinear optical effect, comprising the steps of mixing synthetic organic polymer with at least one compound according to claims 1 or 9.

* * * * *